(12) United States Patent
Barrett et al.

(10) Patent No.: US 10,207,271 B2
(45) Date of Patent: Feb. 19, 2019

(54) BENCHTOP NUCLEIC ACID LIBRARY PREPARATION DEVICE AND METHODS FOR USING THE SAME

(71) Applicant: GenCell Biosystems Ltd., Raheen, County Limerick (IE)

(72) Inventors: Brian Barrett, Cashel (IE); Noel Sirr, Ballymoe (IE); Brian Chawke, Askeaton (IE); Kieran Curran, Ballyclough (IE); John Daly, Tralee (IE)

(73) Assignee: GENCELL BIOSYSTEMS LTD., Raheen, County Limerick (IE)

( * ) Notice: Subject to any disclaimer, the term of this patent is extended or adjusted under 35 U.S.C. 154(b) by 142 days.

(21) Appl. No.: 15/319,365

(22) PCT Filed: Aug. 3, 2015

(86) PCT No.: PCT/IB2015/055904
§ 371 (c)(1),
(2) Date: Dec. 15, 2016

(87) PCT Pub. No.: WO2016/020839
PCT Pub. Date: Feb. 11, 2016

(65) Prior Publication Data
US 2017/0120250 A1 May 4, 2017

Related U.S. Application Data

(60) Provisional application No. 62/032,976, filed on Aug. 4, 2014, provisional application No. 62/032,906, filed
(Continued)

(51) Int. Cl.
*B01L 3/00* (2006.01)
*B01L 7/00* (2006.01)
(Continued)

(52) U.S. Cl.
CPC .............. *B01L 7/52* (2013.01); *B01J 19/0046* (2013.01); *B01L 3/50851* (2013.01);
(Continued)

(58) Field of Classification Search
CPC .... B01L 7/52; B01L 3/50853; B01L 3/50851; B01L 2300/044; B01L 2300/021;
(Continued)

(56) References Cited

U.S. PATENT DOCUMENTS 8,465,707 B2   6/2013  Curran et al.
2003/0082551 A1*  5/2003  Zarling .............. C12N 15/1079
                                                         435/6.16
(Continued)

FOREIGN PATENT DOCUMENTS

EP         0976448 A1      2/2000
WO    WO 2012/011091 A2    1/2012
(Continued)

OTHER PUBLICATIONS

GenCell Biosystems Ltd. "Experience the Lowest Cost Library Prep With Time and Labor Savings", CLiC LP™ Brochure, Feb. 1, 2014, 2 pages. Retrieved from the Internet on Oct. 15, 2015: http://cliclp.com/images/Documents_PDFs/GenCell_Biosystems_CLiC_LP_Overview_0214..pdf.
(Continued)

*Primary Examiner* — Lore R Jarrett
(74) *Attorney, Agent, or Firm* — Kathleen Y. Rao; Bret E. Field; Bozicevic, Field & Francis LLP

(57) ABSTRACT

Complete nucleic acid library preparation devices are provided. Aspects of the devices include: a thermal chip module comprising multiple CLC reaction wells; one or more plate locations; a robotically controlled liquid handler configured to transfer liquid between the one or more plate locations and the thermal chip module; and a bulk reagent dispenser
(Continued)

Sample Cartridge

- Single sample per cartridge – user pipettes 3-10uL nucleic acid sample
- Each sample cartridge contains genetic barcode in CLC
- 2D Barcode for traceability
- Non-assymetric design to ensure correct loading
- Easy tear away seal configured to access each CLC reaction well of the thermal chip module.

19 Claims, 9 Drawing Sheets

Related U.S. Application Data on Aug. 4, 2014, provisional application No. 62/032,961, filed on Aug. 4, 2014, provisional application No. 62/032,899, filed on Aug. 4, 2014, provisional application No. 62/032,901, filed on Aug. 4, 2014.

(51) Int. Cl.
*B01J 19/00* (2006.01)
*C12Q 1/6806* (2018.01)

(52) U.S. Cl.
CPC ........ *B01L 3/50853* (2013.01); *C12Q 1/6806* (2013.01); *B01J 2219/00308* (2013.01); *B01J 2219/00315* (2013.01); *B01J 2219/00369* (2013.01); *B01J 2219/00466* (2013.01); *B01J 2219/00549* (2013.01); *B01J 2219/00585* (2013.01); *B01J 2219/00691* (2013.01); *B01J 2219/00722* (2013.01); *B01L 2300/021* (2013.01); *B01L 2300/044* (2013.01)

(58) Field of Classification Search
CPC .. B01L 9/527; B01L 3/502715; B01L 3/5025; B01L 2300/0636; B01L 2200/0689; B01L 2300/0877; B01L 2300/1844; B01L 9/523; B01L 2300/1827; B01L 3/502707; B01L 2200/025; C12Q 1/6806; C12Q 1/6827; B01J 19/0046; B01J 2219/00722; B01J 2219/00585; B01J 2219/00549; B01J 2219/00466; B01J 2219/00369; B01J 2219/00315; B01J 2219/00308; B01J 2219/00691

See application file for complete search history.

(56) References Cited

U.S. PATENT DOCUMENTS

| | | | |
|---|---|---|---|
| 2004/0029258 A1* | 2/2004 | Heaney | B01L 3/5025 435/287.2 |
| 2015/0238920 A1 | 8/2015 | Curran et al. | |
| 2016/0033370 A1 | 2/2016 | Barrett et al. | |

FOREIGN PATENT DOCUMENTS

| | | |
|---|---|---|
| WO | WO 2012/024658 A2 | 2/2012 |
| WO | WO 2013/111016 A2 | 8/2013 |
| WO | WO 2014/083435 A2 | 6/2014 |
| WO | WO 2014/188281 A2 | 11/2014 |
| WO | WO 2014/207577 A2 | 12/2014 |
| WO | WO 2015/075560 A2 | 5/2015 |
| WO | WO 2015/075563 A2 | 5/2015 |
| WO | WO 2015/120398 A2 | 8/2015 |
| WO | WO 2016/020837 A1 | 2/2016 |
| WO | WO 2016/020838 A1 | 2/2016 |

OTHER PUBLICATIONS

Yuzuki, Dale: "Gen Cell Biosystems' CLiC NGS Library liquid handler at AGBT 2014", Next Generation Technologist, Feb. 20, 2014, 5 pages. Retrieved from the Internet on Oct. 15, 2015: http://www.yuzuki.org/gencell-biosystems-ngs-library-liquid-handler-agbt-2014/.

\* cited by examiner

Thermal Chip Module

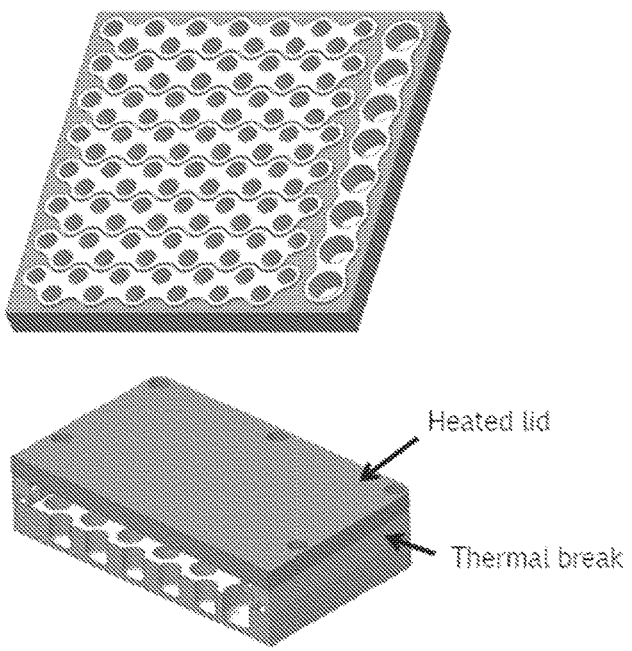

FIG. 1

Consumable Reagent Cartridge

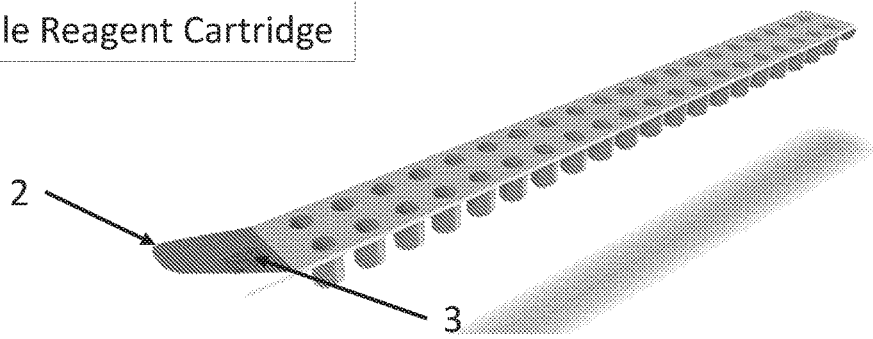

- Generic design that meets requirements for all major protocols
- At least 2 samples per strip (more samples possible for less complex protocols)
- Wells can accommodate CLC's and bulk volumes
- 2D Barcode for traceability
- Non-assymetric design to ensure correct loading
- Tear away seal after loading to masterblock

FIG. 2

Sample Cartridge

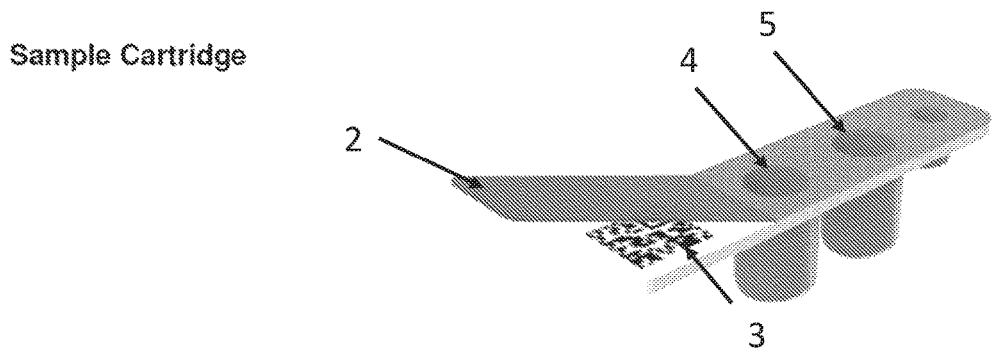

- Single sample per cartridge – user pipettes 3-10uL nucleic acid sample
- Each sample cartridge contains genetic barcode in CLC
- 2D Barcode for traceability
- Non-assymetric design to ensure correct loading
- Easy tear away seal

FIG. 3

Cartridge Masterblock

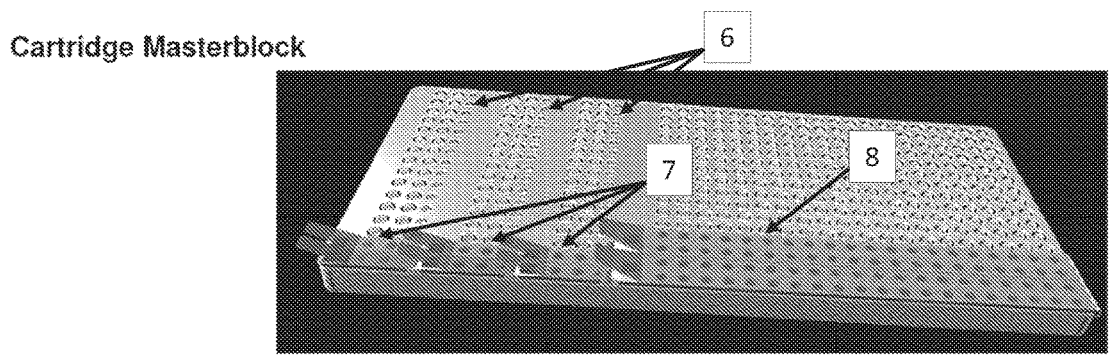

- Removable masterblock to allow user to load cartridges outside of the instrument
- Various master block design's possible for maxium flexibility
- Aluminium block cooled to 10°C when loaded to the deck
- Positioning features to ensure masterblock is accurately loaded

FIG. 4

1.2 H-Gantry Motion

Provides X and Y motion for fluidic heads 1.3 Z-axis Motion

Provides Z axis movement for the Sample Dispensing Head, and for the Purification Head.

The Purification Head has an inbuilt actuator to engage/disengage magnets against the tube walls.

BENCHTOP NUCLEIC ACID LIBRARY PREPARATION DEVICE AND METHODS FOR USING THE SAME

CROSS-REFERENCE TO RELATED APPLICATIONS

Pursuant to 35 U.S.C. § 119 (e), this application claims priority to the filing date of U.S. Provisional Patent Application Ser. No. 62/032,899, filed Aug. 4, 2014, U.S. Provisional Patent Application Ser. No. 62/032,901, filed Aug. 4, 2014, U.S. Provisional Patent Application Ser. No. 62/032,906, filed Aug. 4, 2014, U.S. Provisional Patent Application Ser. No. 62/032,961, filed Aug. 4, 2014, U.S. Provisional Patent Application Ser. No. 62/032,976, filed Aug. 4, 2014 the disclosures of each of which applications are hereby incorporated by reference herein in their entirety.

INTRODUCTION

Composite liquid cell (CLC) technology is a relatively recent platform technology that is highly suitable for carrying out precise biochemical reactions in small working volumes. One practical application of CLC technology is the production of nucleic acid libraries for next generation sequencing (NGS). Library preparation is a process by which a genomic nucleic acid sample is prepared for analysis via next generation sequencing. At present, next-generation platforms use slightly different methodologies such as pyrosequencing, sequencing by synthesis or sequencing by ligation. Most platforms, however, require nucleic acid preparations prior to sequencing. Typical steps include fragmentation (sonication, nebulization or shearing), followed by DNA repair and end polishing (blunt end or A overhang) and, finally, platform-specific adaptor ligation. Even for today's state-of-the-art sequencers a relatively high local concentration of the target molecule is required to sequence accurately. To streamline a particular workflow, automated machinery must overcome the challenges associated with automating and miniaturizing a series of processes aimed at modifying and amplifying nucleic acid content. This biochemistry process is generally performed in 96 or 384 static well plates with typical volumes ranging from 10 microliters to 200 microliters.

SUMMARY

Complete benchtop devices that employ CLC technology for the production of nucleic acid libraries and methods of use thereof are provided. The devices find use in, among other applications, CLC mediated nucleic acid library generation protocols, e.g., for use in next generation sequencing applications.

Aspects of the present disclosure include a complete bench-top nucleic acid library preparation device, the device comprising: a thermal chip module configured to receive a composite liquid cell (CLC) reaction cartridge; a consumable reagent location configured to receive a CLC nucleic acid library preparation reagent cartridge; a sample location configured to receive a CLC sample cartridge; and a robotically controlled liquid handler configured to transfer liquid between the consumable reagent location, the sample location, and the thermal chip module.

In certain embodiments, the device further comprises a magnetic nucleic acid library purification system.

In certain embodiments, the device further comprises a magnetic bead trough.

In certain embodiments, the CLC reaction cartridge comprises from 1 to 100 wells.

In certain embodiments, the device comprises a mechanically actuated lid for the thermal chip module.

In certain embodiments, the CLC nucleic acid library preparation reagent cartridge comprises from 1 to 50 CLC nucleic acid library reagent columns, wherein each column comprise a set of nucleic acid library reagents used to prepare a nucleic acid library from a single sample.

In certain embodiments, each CLC nucleic acid library reagent column comprises from 1 to 30 CLC nucleic acid library reagent wells.

In certain embodiments, the CLC sample cartridge comprises a well for receiving a sample provided by a user and a well comprising a CLC nucleic acid barcoding reagent.

In certain embodiments, the consumable reagent location and the sample location are present on a single cartridge master block.

In certain embodiments, the cartridge master block is removable from the device.

In certain embodiments, the device further comprises a cartridge master block cooling system.

In certain embodiments, the device is operatively coupled to a handheld barcode scanner.

In certain embodiments, the device further comprises a bulk reagent reservoir comprising one or more additional reagents for preparing a nucleic acid library, wherein the robotically controlled liquid handler is further configured to transfer liquid between the bulk reagent reservoir and other locations within the device.

In certain embodiments, the consumable reagent location and the sample location are configured to receive a cartridge comprising wells having a diameter of form 1.0 mm to 8.0 mm and a depth of from 3 mm to 12 mm.

In certain embodiments, the cartridge has a pitch of from 4 mm to 5 mm between the wells.

In certain embodiments, the device is configured to prepare a nucleic acid library from 1 nl to 50 ul of a sample.

In certain embodiments, the reagent volume in the wells of the CLC nucleic acid library preparation reagent cartridge is from 1 nl to 10 ul.

In certain embodiments, the device further comprises a fluidics module comprising liquid reservoirs for system fluids and waste collection.

In certain embodiments, the CLC sample cartridge comprises a CLC sample well and a CLC sample barcode well.

In certain embodiments, the device is configured to produce from 1 to 50 nucleic acid libraries via a CLC mediated protocol.

In certain embodiments, the device is from 35 to 100 cm deep, 35 to 100 cm wide and 25 to 100 cm high.

Aspects of the present disclosure include a method of producing a nucleic acid library from an initial nucleic acid sample, the method comprising: introducing the nucleic acid sample into a device according to any of Claims 1 to 20; and obtaining the nucleic acid library from the device.

In certain embodiments, the nucleic acid library comprises a barcoded nucleic acid library.

In certain embodiments, the nucleic acid library comprises a pooled barcoded nucleic acid library.

In certain embodiments, the nucleic acid library is configured for sequencing by a next generation sequencing protocol.

BRIEF DESCRIPTION OF THE FIGURES

The invention may be best understood from the following detailed description when read in conjunction with the accompanying drawings. Included in the drawings are the following figures:

FIG. 1 provides a schematic diagram of a thermal chip module with reaction cartridges therein according to aspects of the present disclosure.

FIG. 2 provides an example of a consumable reagent cartridge according to aspects of the present disclosure.

FIG. 3 provides an example of a sample cartridge according to aspects of the present disclosure.

FIG. 4 provides an example of a cartridge master block according to aspects of the present disclosure.

DETAILED DESCRIPTION

Figure 5:
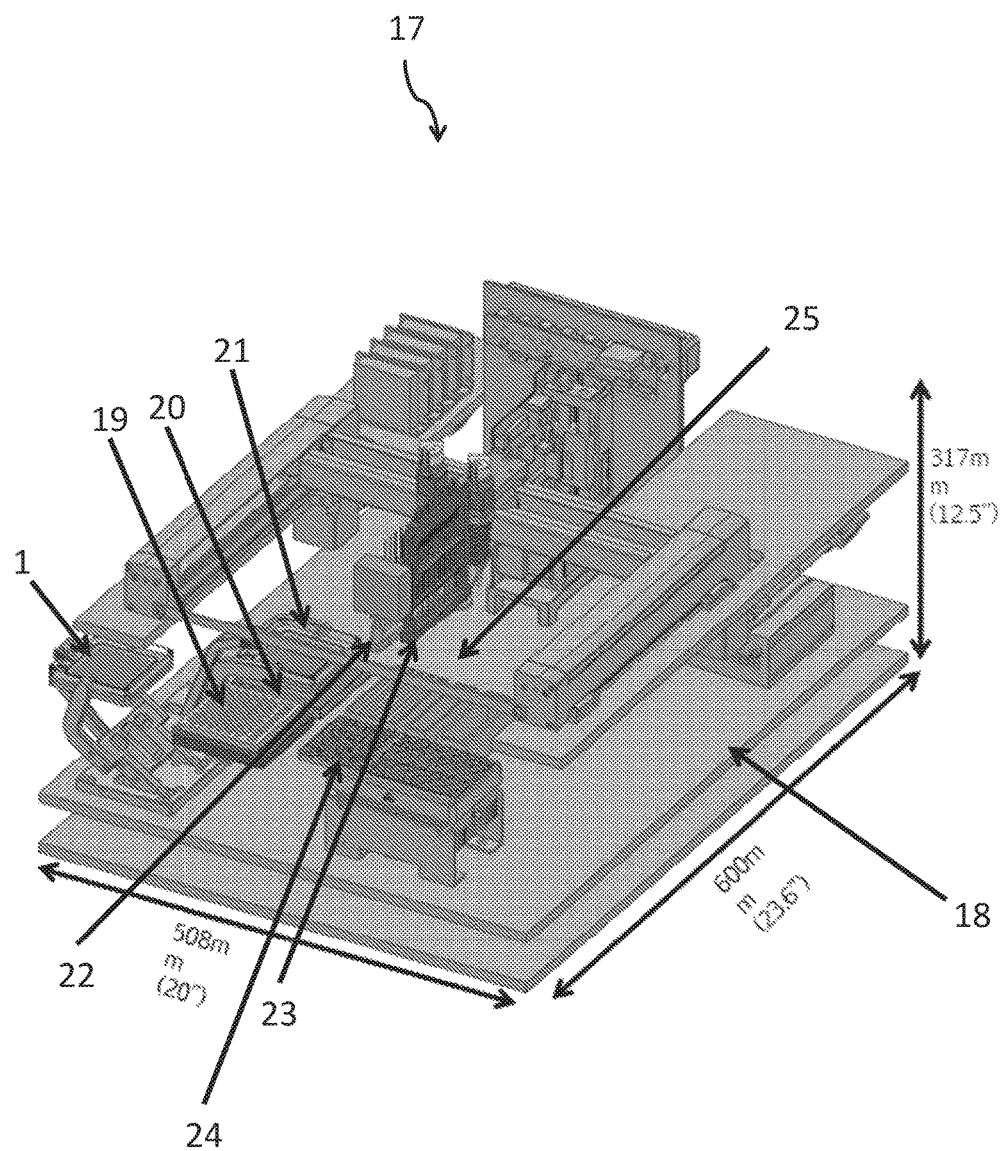
FIG. 5 provides a three-dimensional illustration of a benchtop device according to aspects of the present disclosure.

Complete devices that employ CLC technology for the production of nucleic acid libraries and methods of use thereof are provided. The devices find use in, among other applications, CLC mediated nucleic acid library generation protocols, e.g., for use in next generation sequencing applications. The devices find use in, among other applications, CLC mediated nucleic acid library generation protocols, e.g., for use in next generation sequencing applications and are compact, e.g., benchtop devices.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Composite Liquid Cells (CLCs)

The devise, cartridges and other components described herein are designed to be used in Composite Liquid Cell-based (CLC-based) methods for the generation of nucleic acid libraries from a starting biological sample containing nucleic acids, where the sample, reagent and reaction wells are all self-contained (e.g., wells). By CLC is meant a triphasic fluid arrangement that is a combination of at least three substantially mutually immiscible fluids having three different densities. The first fluid is a carrier fluid which is the densest of the three substantially mutually immiscible fluids; the second fluid is an encapsulating fluid which is the least dense of the substantially mutually immiscible fluids; and the third fluid is a target fluid (sometimes referred to as a "sample") which has a density that is less than the first fluid and greater than the second fluid. A CLC may take a variety of different forms in a self-contained vessel (e.g., as described in greater detail below), where in some embodiments the target fluid is encased in the encapsulating fluid and where the resulting roughly spherical structure is present on the surface of the carrier fluid. In this form, the carrier fluid is not fully covered by the encapsulating fluid. In other embodiments, the target fluid is encased (or encapsulated) between the carrier fluid and the encapsulating fluid such that entire surface of the carrier fluid in the CLC reaction well is covered by the encapsulating fluid.

In certain embodiments, the target fluid is an aqueous fluid, where in some embodiments the aqueous fluid contains a biological sample, reagent, buffer, or other prescribed element of a genetic assay. Examples of components that can be present in the aqueous fluid include, but are not limited to: cells, nucleic acids, proteins, enzymes, biological sample (e.g., blood, saliva, etc.), buffers, salts, organic material, and any combination thereof.

In certain embodiments, the density of the carrier fluid is from 1,300 to 2,000 kg/m$^3$, the density of the target fluid is from 900 to 1,200 kg/m$^3$, and the density of the encapsulating fluid is from 700 to 990 kg/m$^3$. The difference in density between the carrier fluid and the target fluid or between the target fluid and the encapsulating fluid is from 50 to 2000 kg/m$^3$. In general, the difference in density between the three substantially mutually immiscible fluids should be sufficient to prevent substantial intermixing between any two of them under the conditions in which they are to be stored and/or used in any downstream process or analytical assay. Additional details regarding carrier, encapsulating and target fluids may be found in U.S. Pat. Nos. 8,465,707 and 9,080,208; as well as United States Patent Application Publication No. 20140371107; and Published PCT Application Nos: WO2014/083435; WO2014/188281; WO2014/207577; WO2015/075563; WO2015/075560; the disclosures of which applications are herein incorporated by reference.

In certain embodiments, the carrier fluid and/or the encapsulating fluid is an oil. For example, in certain embodiments, the carrier and/or the encapsulating fluid can be a silicone oil, a perfluorocarbon oil, or a perfluoroporyether oil. Thus, in certain embodiments, the carrier fluid is selected from fluorocarbonated oils. In certain embodiments, the encapsulating fluid is selected from silicone oils.

In embodiments in which the target fluid is an aqueous fluid, for example, a biological sample or an aqueous reagent, an example of a CLC includes one in which the carrier (first) fluid is Fluorinert FC-40 (fluorocarbonated oil) having a density of approximately 1,900 kg/m$^3$, the second fluid is a phenylmethylpolvsiloxane (silicone oil) having a density of approximately 920 kg/m$^3$, and the target fluid (sample) is an aqueous-based solution of biological components with a density of approximately 1000 kg/m$^3$.

In certain embodiments, the volume of the target fluid (sample) in the CLC is from about 10 nanoliters (nL) to about 20 microliters (μL). As such, in certain embodiments, the volume of the sample is about 10 nL, about 20 nL, about 30 nL, about 40 nL, about 50 nL, about 60 nL, about 70 nL, about 80 nL, about 90 nL, about 100 nL, about 200 nL, about 300 nL, about 400 nL, about 500 nL, about 600 nL, about 700 nL, about 800 nL, about 900 nL, 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, or about 20 μL.

The volume of the carrier and encapsulating fluid in a CLC should be sufficient to generate a composition in which the target fluid can be fully encapsulated between these fluids when present in a desired CLC reaction well. By fully encapsulated is meant that the target fluid is in direct contact with only the encapsulating fluid and/or the carrier fluid. Thus, the target fluid is not in contact with either the bottom of the CLC reaction well (generally below the carrier fluid) or to the ambient environment (generally above the encapsulating fluid). The amount of fluid is thus dependent not only on the volume of the target fluid, but also on the interior dimensions of the CLC reaction well. While the volume of carrier and encapsulating fluid can vary greatly, in certain embodiments, the volume of the carrier fluid or the encapsulating fluid in the CLC is from about 1 μL to about 100 μL. As such, in certain embodiments, the volume of the carrier fluid or the encapsulating is about 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, about 20 μL, about 25 μL, about 30 μL, about 35 μL, about 40 μL, about 45 μL, about 50 μL, about 55 μL, about 60 μL, about 65 μL, about 70 μL, about 75 μL, about 80 μL, about 85 μL, about 90 μL, about 95 μL, or about 100 μL.

It is noted here that certain wells provided in a cartridge for use in the disclosed devices contain carrier and encapsulating fluids but not a target fluid. In such cases, either a target fluid will be added to the well at some point during the running of the protocol or the carrier and/or encapsulating fluids will be moved to a another well during at some point during the running of the protocol. For example, a well of a sample cartridge (described below) when provided to a user may only include a carrier and encapsulating fluid to which the user adds a sample from which a nucleic acid library is formed. Thus, the context of use of the term CLC should be taken into consideration when referring to wells or series of wells containing CLCs.

Devices

As summarized above, aspects of the invention include a complete, compact nucleic acid NGS library preparation device. As the devices are complete nucleic acid library preparation devices, they include all components necessary to prepare a nucleic acid library suitable for next generation sequencing (NGS) from an initial nucleic acid sample and reagents, e.g., provided in corresponding cartridges. Accordingly, the devices are configured such that an initial nucleic acid sample and reagents can be introduced into the device and a complete nucleic acid library ready for use in a next generation sequencing protocol can be obtained from the device, with little if any user interaction with the device between the time of sample introduction and product NGS library retrieval. The devices include all liquid handling and other components necessary to produce an NGS nucleic acid library, as reviewed in greater detail below. The devices are automated, in that they are configured so that at least some, if not all, steps of a given library preparation protocol may occur without human intervention, beyond introduction of the nucleic acid sample into the device, loading of any requisite reagents (e.g., in cartridge form) and input of information, and activating the device to produce the nucleic acid library from the nucleic acid sample. Steps of a nucleic acid production protocol that may be automated in the devices include, but are not limited to: liquid transfer steps, reagent addition steps, thermal cycling steps, product purification steps, etc.

As indicated above, the devices are compact. By "compact" is meant that the device is dimensioned to be positioned on a bench top or table top in a research laboratory environment. In some instances the device has a depth ranging from 40 to 70 centimeters, such as 42 to 60 centimeters, e.g., 45 centimeters; a width ranging from 35 to 60 centimeters, such as 32 to 50 centimeters, e.g., 40 centimeters; and a height ranging from 25 to 50 centimeters, such as 28 to 40 centimeters, e.g., 30 centimeters. The weight of the device may vary, and in some instances ranges from 20 to 100 kg, such as 40 to 80 kg, e.g., 50 kg.

As summarized above, devices according to embodiments of the invention include at least a thermal chip module configured to receive a composite liquid cell (CLC) reaction cartridge; a consumable reagent location configured to receive a CLC nucleic acid library preparation reagent cartridge; a sample location configured to receive a CLC sample cartridge; and a robotically controlled liquid handler configured to transfer liquid between the consumable reagent location, the sample location, and the thermal chip module. Each of these components or subunits of the device will now be described in greater detail.

Thermal Chip Module

As summarized above, devices described herein include a thermal chip module configured to receive a composite liquid cell (CLC) reaction cartridge. The devices may include a single thermal chip module, or two thermal chip modules. Thermal chip modules are plate or chip type structures that include one or more nodes (or well locations), where the configuration of the nodes accommodates one or more CLC reaction cartridges that contain one or more CLC reaction wells, e.g., a plurality of CLC reaction wells, e.g., from 1 to 400 wells, including 10 to about 400 wells or 1 to 100 wells, e.g., 15 wells, 20 wells, 30 wells, 40 wells, 48 wells, 96 wells, 384 wells, etc. CLC reaction wells are those that are configured to receive a CLC reaction. The volume defined by a given CLC reaction well may vary, and in some instances ranges from 2 µl to 1 ml, such as 5 µl to 20 µl. The cross-sectional shape of a given CLC reaction well may also vary, where cross-sectional shapes of interest include, but are not limited to, cylindrical, conical, frustoconical, circular, rectangular (including square), triangular, etc. While the dimensions of each CLC reaction well may vary, in some instances the CLC reaction wells have a longest cross-sectional dimension (e.g., diameter) ranging from 1 mm to 25 mm, such as 1.0 mm to 10 mm, including 1 to 8 mm and 2.5 to 10 mm, and a depth ranging from 1 mm to 30 mm, such as 3 to 12 mm.

As mentioned above, each CLC reaction well is configured to accommodate a carrier fluid, a target fluid, and an encapsulating fluid that together form a CLC.

An aspect of the thermal chip modules is that they are thermally controlled, such that the temperature of the environment defined by each node (and therefore experienced by a CLC reaction well therein) may be controlled, e.g., including precisely controlled, e.g., to a tenth of degree or better. The range of temperature control may vary, where in some instances the temperature may be controlled between 4 to 120° C., such as 4 to 98° C. To provide for thermal control, the thermal chip module may include heating and/or cooling elements. For example, the thermal chip module may include a cooling region configured to be operably attached to temperature modulator, e.g., a thermoelectric module, a fluidic cooling system or a forced convection cooling system. The chip module may also include a heating element, for example, an etched foil heater electrically connected to a controller, the controller being programmed to activate the heating element to generate a desired thermocycle in the CLCs accommodated therein. An example of a thermal chip module is shown in FIG. 1 (top), which includes positions for multiple CLC reaction cartridges, including a bulk well (right side) that finds use in performing mixing operations where desired (e.g., combining multiple CLC reactions/reagents).

Figure 6:
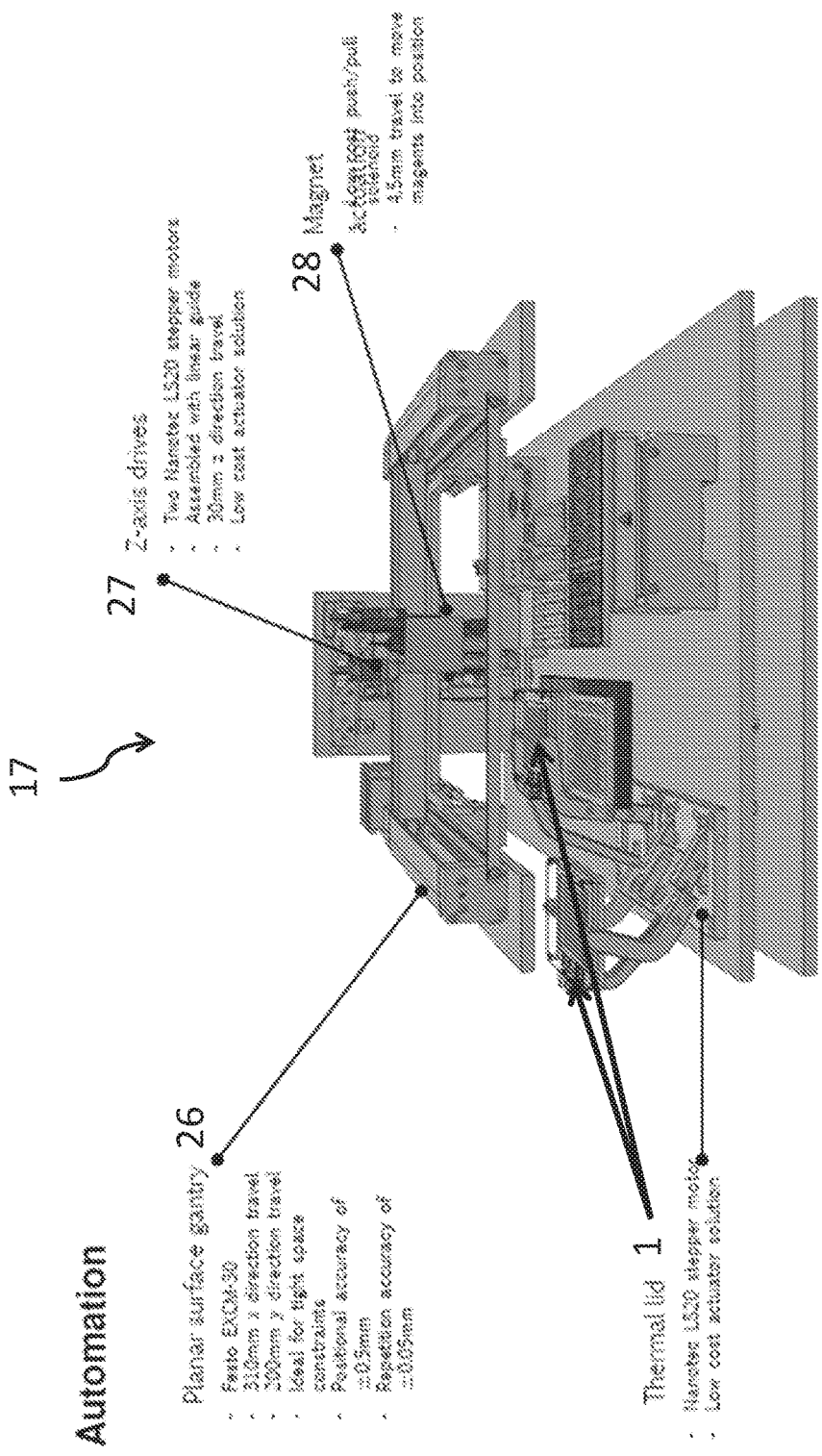
FIG. 6 provides a three-dimensional illustration of a benchtop device according to aspects of the present disclosure with certain automation features indicated.
Figure 7:
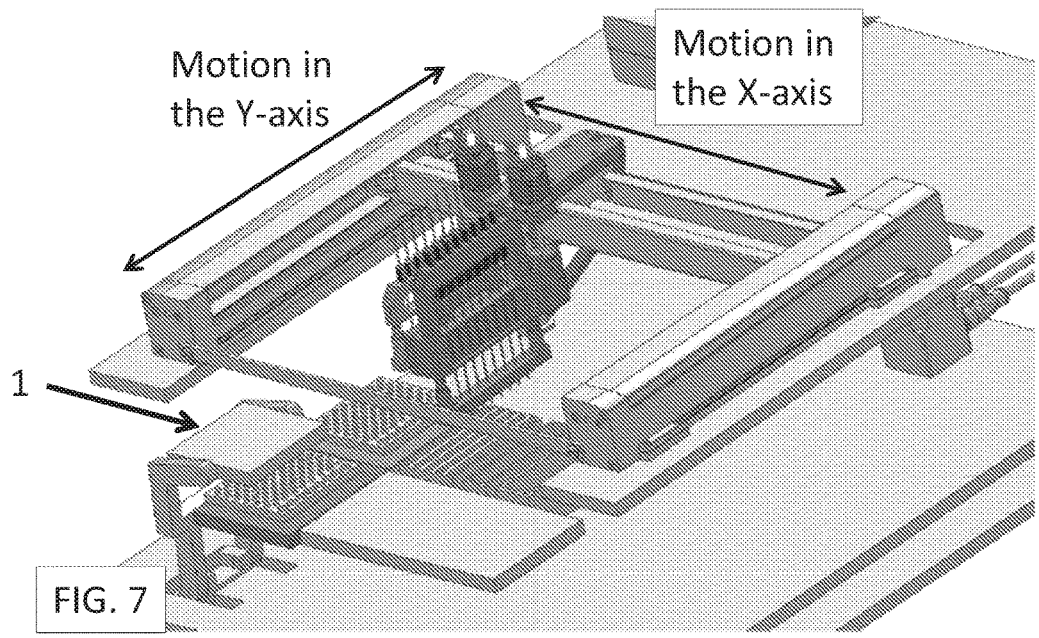
FIG. 7 provides an overhead view of the gantry which provides XYZ movements of the fluidic heads.

The thermal chip module can also be operatively coupled to a lid sized and shaped to mate with the module or portion thereof, e.g., well-defining cartridge, so as to enclose the wells and any CLCs accommodated therein (shown in FIG. 1, bottom). The lid may be openable and closeable by an automatic actuator, or may be manually operated. The lid can seal the carrier liquid into the vessel in order to inhibit evaporation of the carrier liquid. The lid can partially seal against the vessel, or it can be substantially airtight, maintaining a pressure seal. The lid can be transparent to any particularly desired wavelength of light, to allow for electromagnetic interrogation of the CLCs. A heating element can be included in the lid, as desired. The lid can be thermally controlled as desired, such that the temperature of the lid may be modulated to a desired value. Examples of thermal block lids are shown in FIGS. 5, 6 and 7 (element 1).

Consumable Reagent and Sample Cartridges and Locations

As summarized above, devices described herein includes one or more consumable reagent cartridge and sample cartridge locations. A given cartridge location may be a simple stage or support configured to hold a specific cartridge. In many embodiments, the configuration of the cartridge location will be such that the cartridge can only operatively engage with the location in the correct orientation, e.g., with a positioning node, post, or other alignment means. The cartridge locations will generally have a planar surface with one or more nodes (or well locations), where the configuration of the nodes accommodates the desired cartridges (similar to the cartridges for the thermal chip module). While the number and configuration of these cartridge locations present in the device may vary, in some instances the device includes 1 to 20 cartridge locations, such as 2 to 15 cartridge locations, e.g., 10 cartridge locations. The cartridge location(s) may be arranged in any convenient manner in the device, where in some instances in which the device includes a plurality of cartridge locations, the plurality of cartridge locations are arranged adjacent to each other.

Cartridge locations are regions or areas of the device configured to hold a specially-designed cartridge that, in some embodiments, includes specific consumable reagents for performing a library production protocol of interest. Consumable reagent and sample cartridges can be configured to have any convenient number of wells, or even a single well, where when more than one well is present they can be arranged in linear strips or in an array format. The wells can hold any convenient amount of fluid or combination of fluids, e.g., a CLC containing an aqueous regent. For example, a cartridge can have from 1 to 400 wells, such as 1 to 100 wells e.g., 15 wells, 20 wells, 30 wells, 40 wells, 48 wells, 96 wells, 384 wells, etc. The volume defined by a well may vary, and in some instances ranges from 2 µl to 1 ml, such as 5 µl to 20 µl.

Each well of a cartridge, either sample or consumable reagent, is designed to either be empty when received by a user or to have a pre-determined fluid/combination of fluids therein, e.g., an aqueous reagent, a carrier fluid, an encapsulating fluid, or any combination of these fluids (e.g., a CLC configuration as defined above). Cartridges have the wells sealed to keep the fluids from leaking out and/or to keep contaminants from entering the wells. The seals are made to be removable by a user when needed for use in a library production process as described herein. A seal can be in any convenient form, e.g., a lid or series of lids or an elongated substantially planar sheet. Seals can be removed from the wells individually or in groups, e.g., a tear away seal that covers all of the wells of a cartridge. Where the wells are in a multiplex format, the cartridge can contain multiple tear away seals that can be removed independently, e.g., such that a first series of wells is used in a first nucleic acid library production process and a second series of wells is used in a second nucleic acid library production process. Specific consumable reagent and sample cartridges and their contents will be described in further detail below.

In some instances, the cartridge location may be thermally modulated, by which is meant that the temperature of the cartridge location may be controllable, e.g., so as to control the temperature of the contents of the cartridge. Any convenient temperature modulator may be employed to control the temperature of the plate location in a desired manner, where temperature modulators that may be employed include those described above in connection with the thermal chip module.

In some instances, a given cartridge location may be configured to be agitated, e.g., where the plate location is a shaker unit. As such, it may include an agitator (e.g., vibrator or shaker component). While the frequency of the movement of the cartridge location provided by the agitator component may vary, in some instances that agitator may be configured to move the cartridge location between first and second positions at a frequency ranging from 1 rpm to 4000 rpm, such as 50 rpm to 2500 rpm, where the distance between the first and second positions may vary, and in some instances ranges from 10 mm to 400 mm, such as 25 mm to 100 mm.

An example of a consumable reagent cartridge is shown in FIG. 2. As can be seen, this reagent cartridge includes two columns of wells each of which is designed to hold reagents for performing a library production protocol for one sample and a tear away seal covering all of the wells (2). In certain embodiments, this reagent cartridge format is used for processing 2 separate samples; cartridges designed for 1 sample or for three or more samples are also contemplated. The cartridge includes a barcode (3) for traceability by the device and user and a tear away seal to be removed by the user when used (e.g., once lace in the device in the correct cartridge location).

An example of a sample cartridge is shown in FIG. 3. This sample cartridge includes two wells; a first for the user to add a sample of interest (4) and a second that has a genetic barcoding reagent (5) that will mark the nucleic acid library generated from the sample with a specific nucleic acid sequence that can be used in downstream processes (e.g., sequencing) to identify the source of the library product. Such genetic barcodes are commonly used in the art. In some instances, genetic barcodes may include sequencing adapter domains or other functional domains as desired. The cartridge includes a barcode (3) for traceability by the device and user and a tear away seal (2) to be removed by the user when used (e.g., once placed in the device in the correct cartridge location). Sample cartridges can be multiplexed such that multiple different samples and multiple different barcodes can be processed.

FIG. 4 shows an example of a cartridge masterblock. In this example, the cartridge masterblock is removable from the device, thus allowing a user to load the consumable reagent and sample cartridges outside of the instrument for convenience. During use outside of the device, the masterblock can be pre-cooled to prevent the reagents/samples from deteriorating or from reactions proceeding. Positioning features (6) on the masterblock prevent misloading of the cartridges. In this example, the masterblock has 16 columns that each accommodate 3 sample cartridges (7) and a consumable reagent cartridge (8). Note that in this configuration, each column of the consumable reagent cartridge can include reagents for more than one library production protocol (e.g., three library production protocols per column).

Figure 11:
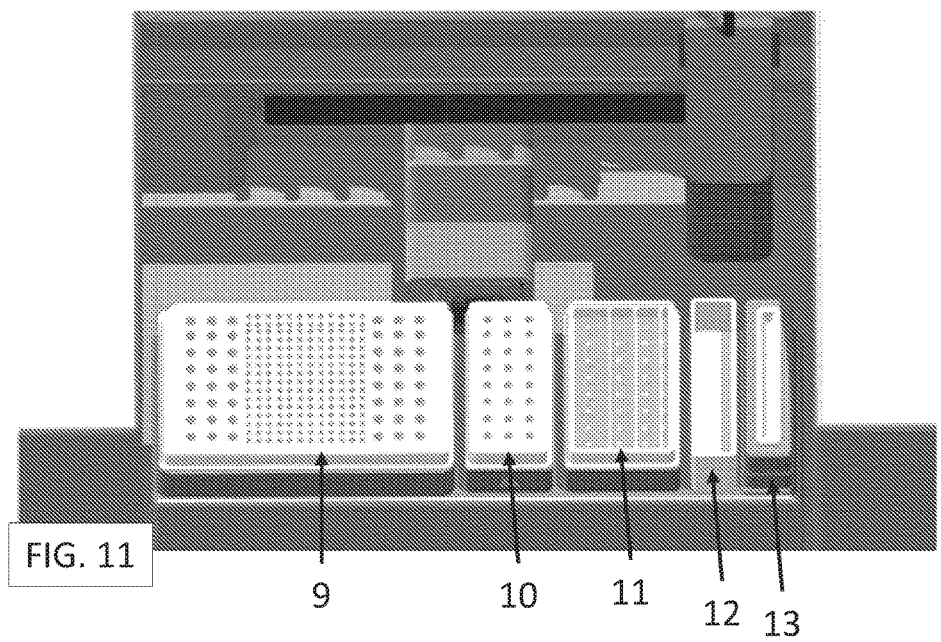
FIG. 11 provides photograph of the troughs, reservoirs, and reaction, sample and reagent cartridge set-up in the device of FIG. 10.

In some embodiments, the sample cartridge and consumable reagent cartridge are combined into a single master cartridge. An example of a master cartridge is shown in FIG. 11 as element (9). This figure also shows examples of additional elements of an embodiment of a device according to aspects of the disclosure, including a CLC reaction cartridge (10) on the thermal chip module, a module to provide a thermally controlled location (11) (e.g., a module that sits at a location in the device that can be maintained at a desired temperature), a wash trough (12), and a magnetic bead suspension well (13) on a shaker.

Figure 12:
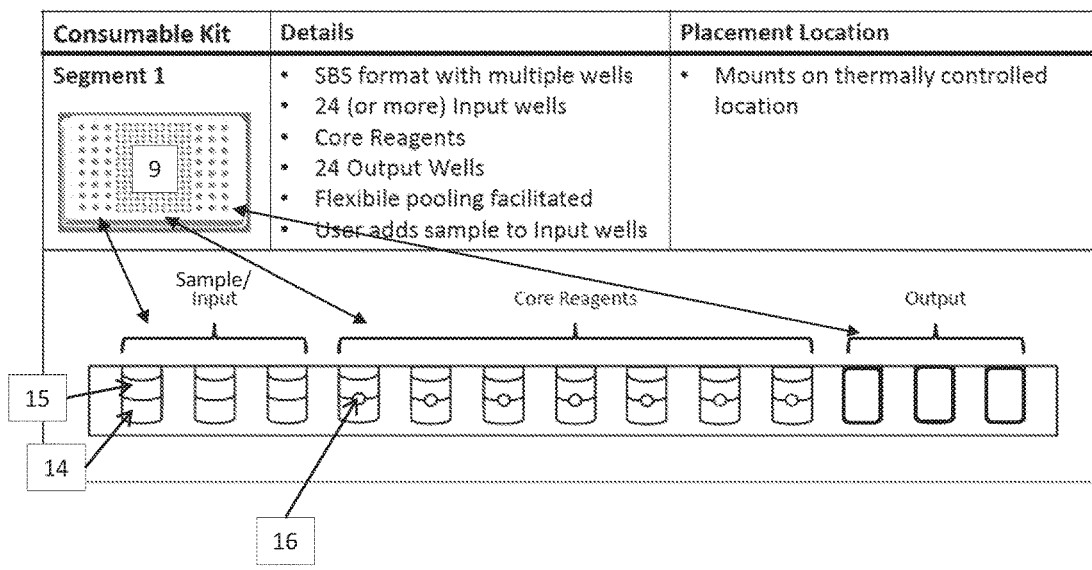
FIG. 12 provides descriptions of the cartridge components shown in FIG. 11.

Some features of the example master cartridge shown in FIG. 11 are described in FIG. 12. As shown in this figure, the master cartridge includes sample/input wells (input wells for samples these are the larger wells positioned on the left), core consumable reagents (or "core reagent") wells in the center, and output wells on the right. As shown, the input wells include carrier (14) and encapsulating (15) fluids such that a CLC is formed when an aqueous sample is added by a user. The reagents in the core reagent wells (16), e.g., aqueous reagents, are provided in a CLC format (i.e., in conjunction with carrier and encapsulating fluids). In some embodiments, the core reagent locations in the master cartridge include a genetic barcoding reagent as would be provided in a separate sample cartridge (as described above). The output wells are empty and are used to receive and hold CLC reactions during the process run or for receiving the final library product once produced at the end of the process run.

FIG. 12 also shows examples of additional cartridges shown in FIG. 11, including a CLC reaction cartridge (10) configured to engage the thermal chip module, a thermally controlled location (11), and a magnetic bead suspension well (13). In the embodiment shown, the CLC reaction cartridge (10) and the module to provide a thermally controlled location (11) are provided in a combined format that can be snapped apart when used (to allow for thermal isolation of the two components). The magnetic bead suspension well provides a location for magnetic beads used for nucleic acid isolation to be held. This component engages with a shaker element in the device to re-suspend the beads prior to loading and transfer processes.

Robotically Controlled Liquid Handler

As summarized above, devices described herein include a robotically controlled liquid handler. The robotically controlled liquid handler is a unit that is configured to transfer liquid and/or CLCs between various locations of the device, such as the sample wells, reagent wells, and the CLC reaction location(s) on the thermal chip module. In a general sense, the robotic liquid handler may be any liquid handling unit that is capable of transferring a quantity of liquid between two distinct locations of the device, such as a reagent well in a reagent cartridge location and a CLC reaction well in a CLC reaction cartridge on a thermal chip module. Robotic liquid handlers of interest are ones that can remove a defined volume of liquid from a first location of the device and deposit that volume of liquid at second location of the device. While the volume of liquid that the handler is configured to transfer may vary, in some instances the volume ranges from 100 nl to 10 ml, such as 100 nl to 1 ml.

In certain embodiments, the liquid handler includes a sample/reagent dispensing head comprising one or more tubes, e.g., capillary tubes, configured to access and transfer liquids from a first well to a second well, or to a reservoir, trough or other receptacle, at any location in the device. The sample/reagent dispensing head can be in fluid communication with a pressure source that can provide positive pressure from any convenient gas, e.g., air, to the tubes/capillary tubes of the dispensing head. Application of the positive pressure can be used to drive an aqueous sample out of the tube/capillary. The system can also include a capillary controller programmed to apply the positive pressure at a desired time so that the liquid sample is dispensed at a predetermined location. Negative pressure may or may not be needed to draw a liquid into the lumen of the tube, as in some instances, capillary action alone will be enough to do so (depending on the liquid and the tube used, e.g., hydrophobicity/hydrophilicity of regions of a capillary tube).

The liquid handler can also include an actuator to move the dispensing head between locations. The actuator can be controlled by a controller, which can be programmed to cause the actuator to move the dispense head. A typical program might first move the distal end of the tube in a dispense head into contact with a sample, draw the sample into the tube, then move the tube so that the distal end is adjacent to a dispensing location, and finally apply sufficient positive pressure to the proximal end of the tube to eject the liquid from the distal end of the tube.

Where capillary tubes are used, the dimensions may vary. In one embodiment, the internal diameter of the capillary tube is about 200 to 250 μm, such as 221 or 230 μm, and the outer diameter is about 800 μm. Any volume of liquid can be chosen to be drawn into the system. Particular capillary tubes may be designed to draw in from about 10 nanoliters to about 10000 nanoliters, such as 500 nanoliters.

In another embodiment, a plurality of capillary tubes are present in the dispense head. The proximal ends of all the capillaries can be in fluid communication with a single pressure conduit, and the pressure conduit in fluid communication with the pressure source. In this way, a single pressure source can be used to apply a single positive pressure to simultaneously dispense liquid from all of the plurality of capillary tubes. Similarly, a single pressure source can apply a single positive pressure to balance the capillary force in all of the plurality of capillary tubes. In such embodiments, the plurality of capillary tubes may be present in a head subunit which includes a holder for the plurality of capillary tubes. The number of capillary tubes in a head subunit may vary, where in some instances the number ranges from 4 to 400, such as 12 to 384, e.g., 24 to 96, including 24 to 48. The capillary tubes may be arranged in the head subunit so that tubes readily align with wells of a laboratory plate when the head is positioned over a laboratory plate, e.g., one that is present on a plate location of the device.

Further details regarding capillary liquid handling systems that may be employed in the device are provided in PCT application Serial No. PCT/IB2013/003145 published as WO 2014/08345; the disclosure of which is herein incorporated by reference.

In some embodiments, the robotic liquid handler includes a purification head, where the purification head is configured to collect and purify nucleic acid libraries produced in the device and dispense them into a desired location/series of locations (e.g., output wells). In some embodiments, the purification head is configured to perform a magnetic bead separation process on a CLC reaction well after the necessary reactions are completed. In certain embodiments, the purification head is configured to deposits an amount of nucleic acid binding magnetic beads into a CLC reaction well, retrieve the CLCs containing the nucleic acid-bound beads from the CLC reaction wells, immobilize the beads, and wash and separate the nucleic acids from the beads using a sequential liquid contact protocol.

In some instances, device includes components for washing the tubes of the dispense and purification heads between liquid handling steps to prevent cross-contamination of the CLC reactions.

Bulk Reagent Reservoir

In certain embodiments, devices described herein include a bulk reagent reservoir. The bulk reagent reservoir includes one or more additional reagents for preparing a nucleic acid library, wherein the robotically controlled liquid handler is further configured to transfer liquid between the bulk reagent reservoir and other locations within the device to deposit a metered volume of a reagent composition, e.g., a liquid reagent composition, into a desired well, e.g., a CLC reagent well on the thermal chip module.

Fluidics Module

Devices described herein may include a fluidics module that includes one or more liquid reservoirs, e.g., for system fluids, waste collection, etc. System fluids of interest include, but are not limited to, wash fluids, elution fluids, etc. Where desired, the waste collection reservoir is operatively coupled to a single waste drain.

Additional Aspects

Devices described herein may be configured to automatically produce large numbers of libraries in a short period of time following commencement of a given library preparation run. The numbers of library samples that the devices may be configured to simultaneously produce ranges in some instances from 1 to 100, such as 4 to 96, e.g., 10, 24, 48 or 96 libraries. While the amount of time required to produce such libraries may vary, in some instances the amount of time ranges from 1 hour to 48 hours, such as 2 to 36 hours, e.g., 6 hours.

To facilitate reagent handling and device set up, the device may include a control processor in operative communication with a handheld unique identifier (e.g., barcode) scanner, which scanner may communicate with the processor via a wired or wireless communication protocol. Such embodiments may be used to upload identifying information regarding laboratory plates and/or reagent sources into the control processor of the device in order configure the device to automatically perform a library preparation protocol.

Specific Embodiment

A specific embodiment of a library preparation device according to the invention is depicted in FIG. 5. FIG. 5 provides an overall view of the internal components of the device (17), i.e., without a cover. Device 17 is compact, at about 600 mm deep, 508 mm wide, and 317 mm high, and weighs less 200 kg or less, such as 100 kg or less, including 50 kg or less. The system is designed to be controlled via a user interface on a typical Windows personal computer on an adjacent bench top. The device shown in FIG. 5 is configured to create DNA libraries using a composite liquid cell (CLC) mediated protocol. The device is configured to create libraries in about 2 to 48 hours using CLCs; operate with a minimum sample census of 1 sample; deliver sample and barcode in multiples of 1 of more.

As shown in FIG. 5, present on main deck (18) are the following sub-components: (a) two independently controlled thermal chip modules (19 and 20); (b) two mechanically actuated lids (1 and 21), one for each thermal chip module (where each lid is thermally controlled and pneumatically actuated); (c) sample and consumable reagent cartridge locations (24; e.g., as a removable cartridge masterblock); (d) locations for additional components (25), including wash reservoirs, magnetic bead suspension well, etc.; and (d) a purification head (23) capable of (i.e., configured for) accessing locations required to purify nucleic acids oa a nucleic acid library generated by the device (e.g., the magnetic bead suspension well); and (e) a sample/reagent dispensing head (22) capable of (i.e., configured for) accessing all wells of the cartridges at each of the thermal chip modules (19 and 20), the sample and consumable reagent cartridges (24), and other liquid handling locations.

Device (17) is designed to accommodate one or more barcoded cartridges (as described above) which are loaded into corresponding locations in the device. Device (17) is configured to accommodate one or more bulk reagent reservoirs when appropriate during a given protocol. Bulk reagents reservoirs include buffers used in CLC reactions, for purification steps, or as wash reagents. In some embodiments, the bulk reagent reservoirs are standard laboratory tubes, e.g., 50 mL tubes, 20 mL tubes, 10 mL tubes, 5 mL tubes, or other test tubes that can be provide to a user, e.g., in a kit, or provide by a user. In some embodiments, bulk reagent reservoirs have barcodes to identify between the different reagents therein, e.g., between buffers and wash reagents. The bulk reagent reservoir locations on the device (not shown in FIG. 5) can be color coded and/or numbered to match corresponding bulk reagent reservoirs and can also have locating features to ensure correct loading into the device.

Device (17) can include a waste drain (not shown) where all fluid waste is pumped to a waste reservoir bottle that can be housed within the device or secured outside of the device. Wash troughs containing wash liquids (placed at location 25) are accessible by the sample/reagent dispensing and purification heads (22 and 23). Wash troughs may be fed automatically from a separately located bulk reagent reservoir. Bulk reagent reservoirs may hold sufficient fluid for one run on the system. Wash bottles may be color coded to aid user loading and avoid error (as noted above).

Figure 8:
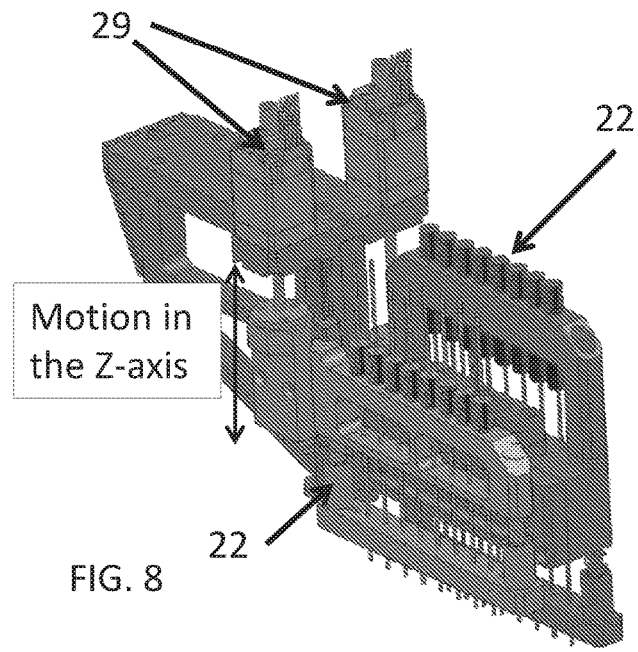
FIG. 8 provides a close-up illustration of a fluidic head.

FIG. 6 provides another view of device (17) detailing certain of the automation elements that are robotically and pneumatically controlled to achieve all necessary functions of the device in generating a nucleic acid library. As shown in FIG. 6, the device includes a planar surface gantry (26) and a Z-axis drives (27) that are configured to be operably connected to the sample/reagent dispensing and purification heads (elements 22 and 23 in FIG. 5) and to move such heads between different locations of the device. Also shown in FIG. 6 are the thermal lids (1) for the thermal chip module, which are activated by a stepper motor, and a magnet (28) for use with the purification head in magnetic bead purification processes. FIG. 7 shows a close-up view of the gantry motion in the X/Y axes while FIG. 8 shows a close-up view of the Z-axis motion for the sample/reagent dispensing head (22) and the purification head (23) (provided by elements 29).

Figure 9:
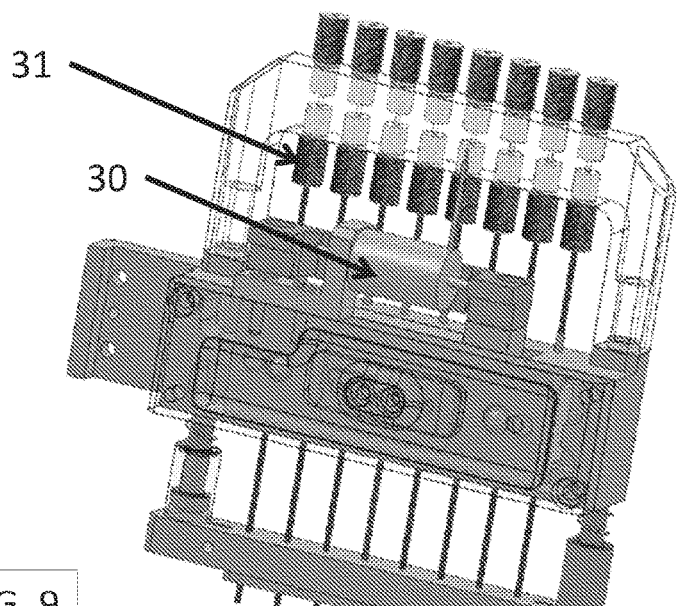
FIG. 9 provides a close-up illustration of a purification head.
Figure 10:
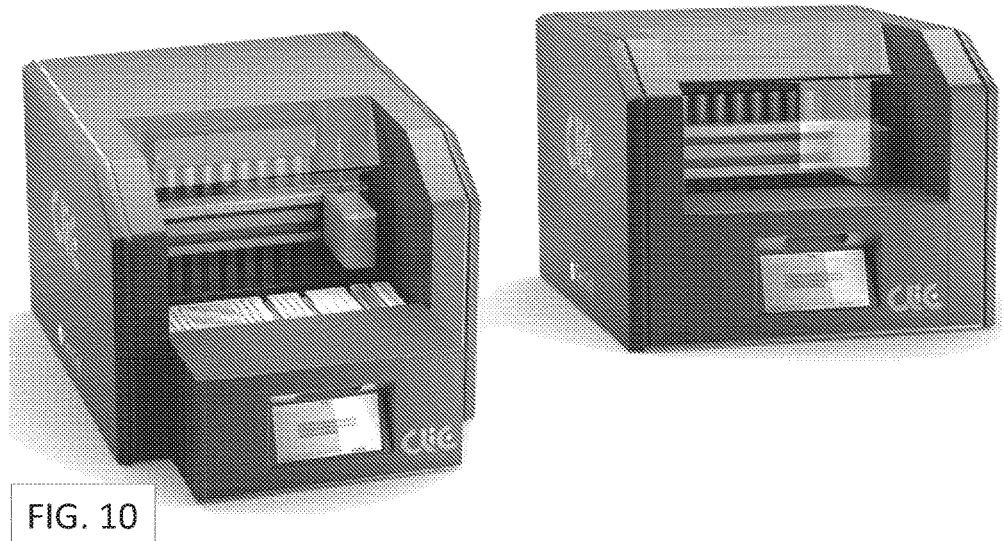
FIG. 10 provides photographs of a benchtop device according to aspects of the present disclosure in open (left) and closed (right) positions.

FIG. 9 provides a view of a purification head which has a built in actuator (30) to encage and disengage the magnets (31) against tube walls.

Figure 13:
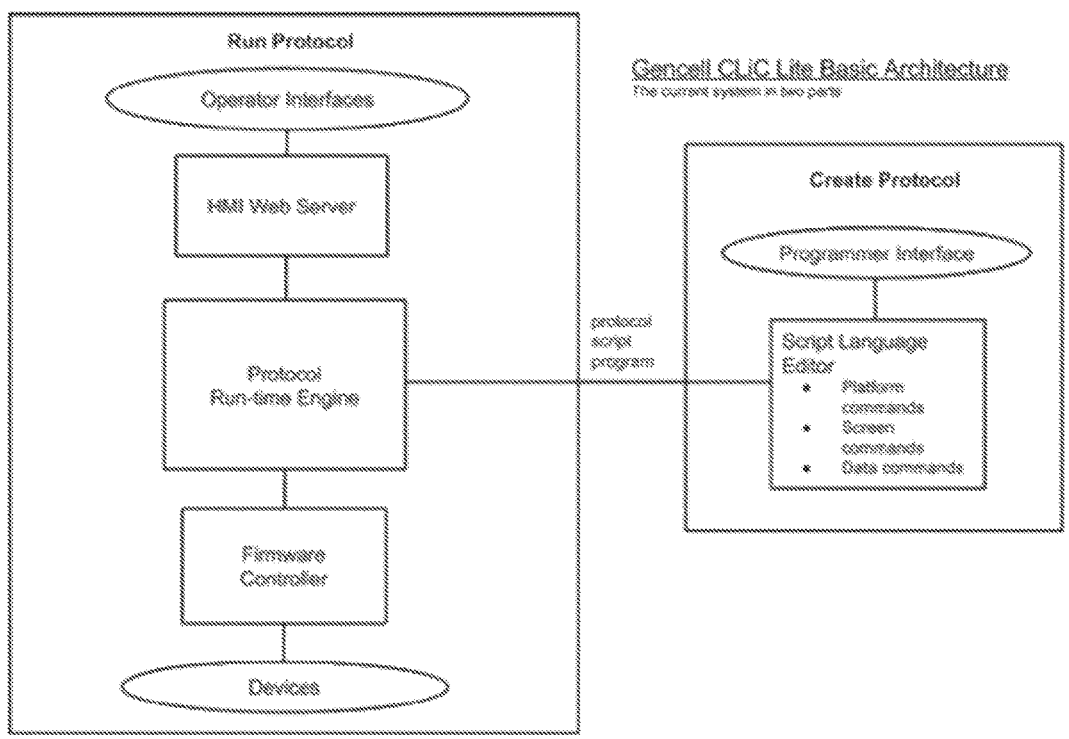
FIG. 13 provides a chart showing an embodiment of how the components of the device are configured to interface with a user and with each other to create and perform a nucleic acid library run protocol.

FIG. 13 provides a chart showing an embodiment of how the components of the device are configured to interface with a user and with each other to create and perform a nucleic acid library run protocol.

Methods of NGS Library Preparation

Aspects of the invention include methods of producing a next generation sequencing (NGS) library from an initial nucleic acid sample by using a device of the invention, e.g., as described above, in a CLC mediated library preparation protocol. The devices of the invention may be employed to produce NGS libraries suitable for sequencing in a variety of different NGS platforms, including but not limited to: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform of interest.

In preparing an NGS library, a nucleic acid sample from which the library is to be prepared is first provided. Any convenient nucleic acid sample preparation method may be employed. Nucleic acid sample preparation may include fragmenting an initial nucleic acid source sample to produce a fragmented nucleic acid sample made up of nucleic acid fragments of suitable size for sequencing with a given NGS sequencing platform. Source nucleic acids of interest include, but are not limited to: deoxyribonucleic acids, e.g., genomic DNA, complementary DNA (or "cDNA", synthesized from any RNA or DNA of interest), recombinant DNA (e.g., plasmid DNA); ribonucleic acids, e.g., messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme; etc.

Source nucleic acids may be fragmented using any convenient protocol, e.g., passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more RNA-shearing enzymes), chemical based fragmentation, e.g., using divalent cations, fragmentation buffer (which may be used in combination with heat) or any other suitable approach for shearing/fragmenting an initial nucleic acid to generate a shorter template nucleic acids suitable for NGS library preparation. In certain aspects, the template nucleic acids generated by shearing/fragmentation of a starting nucleic acid sample has a length of from 10 to 20 nucleotides, from 20 to 30 nucleotides, from 30 to 40 nucleotides, from 40 to 50 nucleotides, from 50 to 60 nucleotides, from 60 to 70 nucleotides, from 70 to 80 nucleotides, from 80 to 90 nucleotides, from 90 to 100 nucleotides, from 100 to 150 nucleotides, from 150 to 200, from 200 to 250 nucleotides in length, or from 200 to 1000 nucleotides or even from 1000 to 10,000 nucleotides, for example, as appropriate for the sequencing platform chosen.

Once prepared, the nucleic acid sample, along with any other samples from which an NGS library is to be prepared in a given run of the device, is placed into a well of a sample cartridge (or sample well of a master cartridge) or analogous container and positioned on a sample cartridge location of the device, e.g., through an open access door of the device. In certain embodiments, the sample cartridge includes a well loaded with a genetic barcode. Also loaded into the device is one or more consumable reagent cartridges comprising the reagents (e.g., buffers, enzymes, adapters, etc.) needed to generate a nucleic acid library form the sample. The consumable reagent cartridge can have a separate well for each different reagent needed for the process in the form of a CLC. Other needed components are also loaded into the device, including purification magnetic beads, library product receptacles (e.g., configured to either maintain individual product libraries or pool two or more different product libraries), bulk reagent reservoirs, wash and purification fluids, etc. In addition, the control instructions and data about a given run may be input into the device, e.g., by using an automated protocol (such as with a hand held barcode scanner) or manually via an appropriate user interface, etc. Control instructions may include the number of samples to be run, which may be input using any convenient protocol, e.g., via manually entered user data or a previously generated .csv file. Information to be input may further include the number of samples and location of samples. The device may include a main user interface. Where desired, the main user interface provides feedback for the following run status information: an animated graphical representation of the main deck showing current action being performed by the liquid handler; a status indicator for each chip indicating its progress through the overall protocol; a countdown timer to the completion of the total run, accurate to +/−10 min; a feedback panel for each chip which will show information pertaining to the current task being performed; a warnings and errors panel where any issues flagged by software will be displayed. The device may further include a web services component, e.g., which is configured to monitor status and generate an email to be sent in the event of a critical error. The system may also be configured to produce an output file: e.g., which may include a barcoding file, and a library definition file, where such files can be optionally amalgamated into one. The name of the run log folder may be included in the output file as well as the protocol that was run. Run logs may be numbered to keep them in order. The device may be configured to guide a user during setup. For example, during run setup a user may be guided through the cartridge loading sequence and prompted to scan the cartridge barcode when appropriate. When a user is required to enter information, the system may prompt a user to select from a number of predefined options within a drop-down list rather than freely entering information. Following device set up, including closure of any open access door or other open component, the device is ready to perform an automated CLC mediated library preparation protocol.

As such, once the device is loaded with nucleic acid sample(s) and configured for a given NGS library production run, the run is started. During the run, the device accesses the sample/reagent dispensing head of the robotic liquid handler to transfer a suitable volume of nucleic acid sample, e.g., 1 nl to 1 ml, such as 1 nl to 50 ul, e.g., 100 nl to 50 ul, from one or more sample wells of a sample cartridge to a CLC reaction well of the thermal chip module. In some embodiments, the sample well in the sample cartridge had carrier and encapsulating fluids therein, such that a CLC was formed when the sample was added to the well, and thus a CLC is formed in the CLC reaction well upon transfer. In other embodiments, the carrier and encapsulating fluids are present in the CLC reaction cartridge and the sample well on contains the nucleic acid sample. Regardless of the configuration, the sample/reagent dispenser head deposits a volume of nucleic acid sample into the CLC reaction well using a non-contact microfluidic dispensing protocol in a manner sufficient to produce a CLC having a sample core. Details regarding CLC production methods which may be employed by the device are further described in U.S. Pat. No. 8,465,707, the disclosure of which is herein incorporated by reference.

Following production of sample containing CLC reaction(s) in corresponding CLC reaction well(s), e.g., from one or more corresponding samples, at the thermal chip module(s), the sample/reagent dispenser accesses the wells of the consumable reaction cartridge to dispense reagents into each CLC reaction well. Reagents that may be dispensed into the different CLC reaction wells by the sample/reagent dispenser include, but are not limited to: dNTPs, enzymes (e.g., polymerases, nucleases, ligases, etc.), primers, platform specific sequencing adaptors (which may or may not be integrated with the primers), etc. The sample/reagent dispenser may employ a non-contact microfluidic dispensing protocol in order to add the reagents to the CLCs. Each reagent may be sequentially added, or two or more reagents may be pre-combined and added to the CLCs, as desired. Following reagent addition to the CLCs in the CLC reaction wells by the sample/reagent dispenser, the thermal chip module(s) may be subjected to temperature modulation, e.g., in the form of thermal cycling, as desired for a given NGS library preparation protocol.

At any step during the process, generally where dictated by the nature of the library production protocol, sample identifiers, e.g., nucleic acid barcodes, may be added to the CLC reaction wells to uniquely identify the nucleic acids in each CLC reaction well according to the sample source. In this step, the sample/reagent dispense head is employed to transfer a volume of barcode reagent from a barcode well, e.g., provided in a sample cartridge or a cartridge masterblock, to a CLC reaction well of the thermal chip module having the corresponding sample-containing CLC present therein. The sample/reagent dispense head deposits a volume of barcode reagent into the CLC reaction well using a non-contact microfluidic dispensing protocol in a manner sufficient to produce a CLC having a sample core that includes a nucleic acid barcode.

The sample/reagent dispenser then dispenses ligase into each CLC reaction well(s), e.g., derived form a specific well in the consumable regent cartridge. The sample/reagent dispenser may employ a non-contact microfluidic dispensing protocol in order to add the ligase to the CLC reaction locations. Following ligase addition to the CLC reaction well(s) by the sample/reagent dispenser, the thermal chip modules may be subjected to thermal cycling, as desired, e.g., to ligate the barcodes to the nucleic acids in the CLCs and thereby produce barcoded nucleic acids.

Following production of the barcoded nucleic acid libraries in the CLCs of the CLC reaction wells in the CLC reaction cartridge present on the thermal chip module(s), the resultant barcoded nucleic acid libraries may be purified to produce a product NGS library suitable for use in an NGS sequencing protocol. While the resultant barcoded libraries may be purified using any convenient protocol, in some instances a magnetic bead based purification protocol is employed. In such a protocol, the purification head of the robotic liquid handler is employed to transfer a suitable quantity of magnetic beads, e.g., 100 nl to 1 ml, from one or more wells of a magnetic bead holder present on a shaker unit location in the device to one or more CLC reaction wells of the thermal chip module. The purification head deposits an amount of magnetic beads into the CLC reaction well using a non-contact microfluidic dispensing protocol in a manner sufficient to produce a CLC that includes magnetic beads. The beads are configured to specifically bind to barcoded nucleic acid library in the CLC, e.g., via complementary nucleic acid domains that hybridize to each other. Following a suitable period of time for specific binding of barcoded nucleic acid library to the beads, the purification head is used to retrieve the CLCs containing the nucleic acid-bound beads from the CLC reaction wells and then separate the nucleic acids from the beads using a sequential liquid contact protocol. In such a protocol, the magnetic beads are first immobilized at a location of a conduit of the purification head (e.g., an inner surface), e.g., by positioning the conduit next to a magnetic field. Next, a wash fluid is flowed past the immobilized beads, which removes CLC encapsulating fluid and other non-bead bound entities from the immobilized beads. Following washing, the bead bound nucleic acid amplicons may be released from the beads by flowing a suitable eluent liquid past the immobilized beads. The resultant released barcoded nucleic acid library may then be collected, including pooled, into suitable receptacles positioned in the device (e.g., in the output wells of a the cartridge masterblock) and are then ready for use in a NGS sequencing protocol. Details regarding magnetic bead/conduit based purification protocols that may be employed by the device are further described in PCT Application Serial No. PCT/IB2014/002159 published as WO 2014/207577; the disclosure of which is herein incorporated by reference.

The resultant product NGS libraries may then be sequenced, as desired, using any convenient NGS sequencing platform, including: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other convenient sequencing platform.

Computer Controllers

Aspects of the present disclosure further include computer controllers for operating the devices, where the controllers further include one or more computer elements for complete automation or partial automation of a device as described herein. In some embodiments, the controllers include a computer having a computer readable storage medium with a computer program stored thereon, where the computer program when loaded on the computer includes instructions for actuation the device to perform a CLC mediated NGS library production protocol, e.g., as described above.

In embodiments, the controller includes an input module, a processing module and an output module. Processing modules of interest may include one or more processors that are configured and automated to implement one or more routines of the device, e.g., as described above. For example processing modules may include two or more processors, such as three or more processors, such as four or more processors and including five or more processors, that are configured and automated to produce an NGS library. As described above, each processor includes memory having a plurality of instructions for performing the steps of the subject methods.

The controllers may include both hardware and software components, where the hardware components may take the form of one or more platforms, such that the functional elements, i.e., those elements of the controller that carry out specific tasks (such as managing input and output of information, processing information, etc.) of the controller may be carried out by the execution of software applications on and across the one or more computer platforms represented of the system.

Controllers may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Pert, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, controllers according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT™, Windows XP, Windows 7, Windows 8, iOS, Sun Solaris, Linux, OS/400, Compaq Tru64 Unix, SGI IRIX, Siemens Reliant Unix, and others.

Notwithstanding the appended clauses, the disclosure set forth herein is also defined by the following clauses:

1. A complete bench-top nucleic acid library preparation device, the device comprising:
a thermal chip module configured to receive a composite liquid cell (CLC) reaction cartridge;
a consumable reagent location configured to receive a CLC nucleic acid library preparation reagent cartridge;
a sample location configured to receive a CLC sample cartridge; and
a robotically controlled liquid handler configured to transfer liquid between the consumable reagent location, the sample location, and the thermal chip module.

2. The device according to Clause 1, further comprising a magnetic nucleic acid library purification system.

3. The device according to Clause 2, further comprising a magnetic bead trough.

4. The device according to any of Clauses 1 to 3, wherein the CLC reaction cartridge comprises from 1 to 100 wells.

5. The device according to any of Clauses 1 to 4, wherein the device comprises a mechanically actuated lid for the thermal chip module.

6. The device according to any of Clauses 1 to 5, wherein the CLC nucleic acid library preparation reagent cartridge comprises from 1 to 50 CLC nucleic acid library reagent columns, wherein each column comprise a set of nucleic acid library reagents used to prepare a nucleic acid library from a single sample.

7. The device according to Clause 6, wherein each CLC nucleic acid library reagent column comprises from 1 to 30 CLC nucleic acid library reagent wells.

8. The device according to any of Clauses 1 to 7, wherein the CLC sample cartridge comprises a well for receiving a sample provided by a user and a well comprising a CLC nucleic acid barcoding reagent.

9. The device according to any of Clauses 1 to 8, wherein the consumable reagent location and the sample location are present on a single cartridge master block.

10. The device according to Clause 9, wherein the cartridge master block is removable from the device.

11. The device according to Clause 9 or 10, further comprising a cartridge master block cooling system.

12. The device according to any of Clauses 1 to 11, wherein the device is operatively coupled to a handheld barcode scanner.

13. The device according to any of Clauses 1 to 12, further comprising a bulk reagent reservoir comprising one or more additional reagents for preparing a nucleic acid library, wherein the robotically controlled liquid handler is further configured to transfer liquid between the bulk reagent reservoir and other locations within the device.

14. The device according to any of Clauses 1 to 13, wherein the consumable reagent location and the sample location are configured to receive a cartridge comprising wells having a diameter of form 1.0 mm to 8.0 mm and a depth of from 3.0 mm to 12 mm.

15. The device according to Clause 14, wherein the cartridge has a pitch of from 4 mm to 5 mm between the wells.

16. The device according to any of Clauses 1 to 15, wherein the device is configured to prepare a nucleic acid library from 1 nl to 50 ul of a sample.

17. The device according to any of clauses 1 to 16, wherein the reagent volume in the wells of the CLC nucleic acid library preparation reagent cartridge is from 1 nl to 10 ul.

18. The device according to any of Clauses 1 to 17, wherein the device comprises a fluidics module comprising liquid reservoirs for system fluids and waste collection.

19. The device according to any of Clauses 1 to 18, wherein the CLC sample cartridge comprises a CLC sample well and a CLC sample barcode well.

20. The device according to any of Clauses 1 to 19, wherein the device is configured to produce from 1 to 50 nucleic acid libraries via a CLC mediated protocol.

21. The device according to any of Clauses 1 to 20, wherein the device is from 35 to 100 cm deep, 35 to 100 cm wide and 25 to 100 cm high.

22. A method of producing a nucleic acid library from an initial nucleic acid sample, the method comprising:
introducing the nucleic acid sample into a device according to any of Clauses 1 to 20; and
obtaining the nucleic acid library from the device.

23. The method according to Clause 22, wherein the nucleic acid library comprises a barcoded nucleic acid library.

24. The method according to Clause 22 or 23, wherein the nucleic acid library comprises a pooled barcoded nucleic acid library.

25. The method according to any of Clauses 22 to 24, wherein the nucleic acid library is configured for sequencing by a next generation sequencing protocol.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A complete bench-top nucleic acid library preparation device, the device comprising:
a thermal chip module configured to receive a composite liquid cell (CLC) reaction cartridge;
a CLC reaction cartridge positioned at the thermal chip module and comprising a plurality of wells;
a consumable reagent location configured to receive a CLC nucleic acid library preparation reagent cartridge;
a CLC nucleic acid library preparation reagent cartridge positioned at the consumable reagent location and comprising a plurality of wells;
a sample location configured to receive a CLC sample cartridge;
a CLC sample cartridge positioned at the sample location and comprising a plurality of wells; and
a robotically controlled liquid handler configured to transfer liquid between the consumable reagent location, the sample location, and the thermal chip module, wherein the thermal chip module, the consumable reagent location, and the sample location are positioned on a main deck of the device, and
wherein at least one well of the CLC reaction cartridge, the CLC nucleic acid library preparation reagent cartridge, or the CLC sample cartridge comprises a carrier fluid and an encapsulating fluid.

2. The device according to claim 1, further comprising a magnetic nucleic acid library purification system comprising a purification head configured to access wells of the device.

3. The device according to claim 2, further comprising a magnetic bead trough.

4. The device according to claim 1, wherein the device comprises a mechanically actuated lid for the thermal chip module.

5. The device according to claim 4, wherein the mechanically actuated lid comprises a heating element.

6. The device according to claim 1, wherein the CLC nucleic acid library preparation reagent cartridge comprises from 1 to 50 CLC nucleic acid library reagent columns, wherein each column comprise a set of nucleic acid library reagents used to prepare a nucleic acid library from a single sample.

7. The device according to claim 6, wherein each CLC nucleic acid library reagent column comprises from 1 to 30 CLC nucleic acid library reagent wells.

8. The device according to claim 1, wherein the CLC sample cartridge comprises a well for receiving a sample provided by a user and a well comprising a CLC nucleic acid barcoding reagent.

9. The device according to claim 1, wherein the consumable reagent location and the sample location are present on a single cartridge master block.

10. The device according to claim 9, wherein the cartridge master block is removable from the device.

11. The device according to claim 1, further comprising a bulk reagent reservoir comprising one or more additional reagents for preparing a nucleic acid library, wherein the robotically controlled liquid handler is further configured to transfer liquid between the bulk reagent reservoir and other locations within the device.

12. The device according to claim 1, wherein the device comprises a fluidics module comprising liquid reservoirs for system fluids and waste collection.

13. A method of producing a nucleic acid library from an initial nucleic acid sample, the method comprising:
introducing the nucleic acid sample into a device according to claim 1; and
obtaining the nucleic acid library from the device.

14. The method according to claim 13, wherein the nucleic acid library comprises a barcoded nucleic acid library.

15. The method according to claim 13, wherein the nucleic acid library comprises a pooled barcoded nucleic acid library.

16. The method according to claim 13, wherein the nucleic acid library is configured for sequencing by a next generation sequencing protocol.

17. The device according to claim 1, wherein the at least one well further comprises an aqueous fluid.

18. The device according to claim 1, wherein the robotically controlled liquid handler is configured to draw and dispense liquid.

19. The device according to claim 1, wherein the CLC nucleic acid library preparation reagent cartridge and the CLC sample cartridge comprise a seal.

* * * * *